United States Patent [19]

Jensen

[11] Patent Number: 5,374,531
[45] Date of Patent: Dec. 20, 1994

[54] IMMUNOASSAY FOR DETERMINATION OF CELLS

[75] Inventor: Bruce D. Jensen, Collegeville, Pa.

[73] Assignee: Zynaxis, Inc., Malvern, Pa.

[21] Appl. No.: 34,138

[22] Filed: Mar. 22, 1993

[51] Int. Cl.$^5$ ............... G01N 33/543; G01N 33/546; G01N 33/553; G01N 33/569

[52] U.S. Cl. ............... 435/7.24; 435/7.32; 435/7.92; 435/975; 436/518; 436/523; 436/526; 436/533; 436/534

[58] Field of Search ............ 435/7.24, 7.2, 34, 39, 435/975, 7.92, 7.32, 7.31; 436/526, 523, 533, 534, 503, 518, 548

[56] References Cited

U.S. PATENT DOCUMENTS

| | | | |
|---|---|---|---|
| 3,970,518 | 7/1976 | Giaever | 436/526 |
| 4,018,886 | 4/1977 | Giaever | 436/526 |
| 4,115,535 | 9/1978 | Giaever | 436/526 |
| 4,376,110 | 3/1983 | David et al. | 435/7.94 |
| 4,486,530 | 12/1984 | David et al. | 436/534 |
| 4,576,912 | 3/1986 | Yaverbaum et al. | 436/526 |
| 4,642,284 | 2/1987 | Cooper et al. | 436/518 |
| 4,731,337 | 3/1988 | Luotola et al. | 436/526 |
| 4,745,077 | 5/1988 | Holian et al. | 436/526 |
| 4,777,145 | 10/1988 | Luotola et al. | 436/526 |
| 5,145,784 | 9/1992 | Cox et al. | 436/526 |

FOREIGN PATENT DOCUMENTS

| | | |
|---|---|---|
| 22948/88 | 4/1989 | Australia. |
| 899017560 | 1/1989 | European Pat. Off.. |
| PCT/FI8600-041 | 4/1986 | WIPO. |
| PCT/GB880-0614 | 7/1988 | WIPO. |
| PCT/US880-3529 | 10/1988 | WIPO. |

OTHER PUBLICATIONS

King, 1984. Simultaneous Detection of Two Cell Surface Antigens by a Red Blood Cell Rosette–Microsphere Binding Methol, and its Application to the Study of Multiple Myeloma J Immunol. Meth. 72:481–8.

Dynal, 1989, Dynabeads M–450 Technical Handbook. Dynal A.S., Oslo.

Brinchmann et al, 1988, Direct Immunomagnetic Quantification of Lymphoctye Subsets in Blood. Clin Exp. Immunol. 71:182–6.

Goding, 1983. *Monoclonal Antibodies: Principles and Practice*, Academc Press, Inc., London. p. 239.

Primary Examiner—David Saunders
Assistant Examiner—James L. Grun
Attorney, Agent, or Firm—Dann, Dorfman, Herrell and Skillman

[57] ABSTRACT

Methods and test kits are provided for the quantitative or qualitative determination of selected analytes, e.g., cell subsets in a mixed cell population, using a particulate separation reagent and a particulate detection reagent. The invention enables cell monitoring of AIDS patients in a efficient and reliable manner.

14 Claims, 4 Drawing Sheets

● Magnetic CD4 Bead
⊗ Fluorescent CD4 Bead

IMMUNOASSAY FOR DETERMINATION OF CELLS

FIELD OF THE INVENTION

The present invention relates to diagnostic testing and in particular to a method for determining the presence or quantity of selected analytes, each having at least one characteristic determinant, within a mixed population of same, and to test kits used in performing such methods. The method of the invention facilitates screening of complex biological fluids, such as whole blood, containing small fractions of particular cell types or subsets of interest, and provides an efficient and reliable assay for cell monitoring of AIDs patients.

DESCRIPTION OF THE PRIOR ART

Methodology for determining components of blood or bone marrow, e.g., subpopulations of leukocytes, is routinely employed in the clinical diagnosis of various pathological conditions. The clinical application of this methodology has been spurred by the general availability of monoclonal antibodies selectively reactive with characteristic determinants of the discrete components of interest. These determinations have proven useful for monitoring changes in immunodeficiency diseases, leukemias, lymphomas and transplant patients. See: A. Landay and K. Muirhead, Clin. Immunol. and Immunopathol., 52: 48–60 (1989). Immunofluorescence labelling followed by flow cytometric analysis or fluorescence microscopy is the established method for performing such determinations.

Flow cytometry has decided advantages over other cell marker analysis techniques of the prior art, such as immunofluorescence microscopy, immunocytochemistry, and enzyme immunoassay. One particular advantage of flow cytometry over bulk methods of marker analysis (e.g., fluorimetry or enzyme immunoassay) is the utilization of multiple detectors to simultaneously analyze multiple signals from each cell. For example, U.S. Pat. No. 4,727,020 to Recktenwald describes the use of two fluorescent channels to detect cells in a subpopulation specifically labelled with two different immunofluorescent agents. U.S. Pat. No. 4,284,412 to Hansen et al. describes the use of fluorescence channels to detect forward and right angle light scatter of cells of different subpopulations in blood. In both cases, at least one parameter is used for gating so that a signal from a cell (e.g., fluorescence from a fluorochrome) is electronically measured only if the cell falls within the gated subpopulation of interest. Such multiparametric measurement is useful for enumerating cell types of interest within a complex population of cells (e.g., whole blood). This method is time consuming, however, since each sample must be analyzed one cell at a time for the parameters of interest.

Clearly, one distinct disadvantage of flow cytometry is that each sample has to be run and analyzed individually. Indeed, current clinical applications of flow cytometry, to a large degree, involve the study of immunologic or neoplastic disorders of peripheral blood, bone marrow or tissue that can be disaggregated into single cell suspension. This disadvantage is particularly acute in a clinical laboratory which must process multiple patient specimens daily. The ability to simultaneously quantitate multiple cell samples, each containing a plurality of cells, as such would substantially reduce the throughput time for such cytometric analysis in the clinical or research laboratory.

One proposed method for analyzing samples comprising a plurality of cells is enzyme-linked immunosorbent assay (ELISA). See: J. Endl. et al., J. Immunol. Meth., 102: 77–83 (1987). See also U.S. Pat. No. 4,876,189 to Shetters et al. This assay measures absorbance of cell samples at one time using a 96-well microplate reader. The reporter system in this assay utilizes an enzyme conjugated to a monoclonal antibody against a specific antigen and cannot distinguish between an antigen on the subset of interest (e.g., CD4 on lymphocytes) and the same antigen on another subset (e.g., CD4 on monocytes). Consequently, this technique is not well-suited to determination of cell subpopulations in whole blood.

Another method for detection of cell surface antigens or antibodies thereto measures agglutination of fluorochrome labelled erythrocytes. V. Ghazarossian et al., Clin. Chem., 34: 1720–25 (1988); see also U.S. Pat. No. 4,748,129. This method has particular application for blood typing or the detection of antibodies to blood group antigens. Fluorochromes are used to label erythrocyte membranes and the presence of the antibodies or antigens is then determined from fluctuations in the fluorescence signal (detected by a fiber optic probe) due to agglutination of the erythrocytes. This system can produce only qualitative or, at best, semi-quantitative results as to the presence or absence of antigens or antibodies of interest. When the assay is employed to measure the presence of antibodies in plasma, erythrocytes in the blood sample are removed by the addition of colloidal magnetite particles and exposure of the sample to a magnetic field.

In diagnostic testing, it is often desirable to sort out and separate for further analysis a cell subpopulation or cell type of interest from a mixed cell population. Affinity separation of cells using protein-coated magnetic particles is known. Various methods for sorting biological populations via magnetic affinity separation have been described in the patent literature and elsewhere. See, for example, U.S. Pat. Nos. 3,970,518, 4,710,472, 4,677,067, 4,666,595, 4,230,685, 4,219,411, 4,517,323; see also, E. T. Menz et al., Am. Biotech. Lab. (1986); J. S. Kemshead et al., Molec. Cell Biochem., 67: 11–18 (1985); T. Leivestad et al., Tissue Antigens, 28: 46–52 (1986); and J. S. Berman et al., J. Immunol., 138: 2100–03 (1987). In performing such methods, a binding molecule (e.g., monoclonal antibody) is typically conjugated to the magnetic particles, and added to a test sample under conditions causing binding to a characteristic determinant on the analyte of interest, after which the test sample is exposed to a magnetic field. See, for example, the immunomagnetic separation technique described by Leivestad et al., supra. The magnetic particles and analyte affixed thereto can then be separated from the rest of the population.

The use of magnetic affinity separation has been reported in clinical diagnostic immunoassays for soluble analytes which utilize a radioisotope (see, for example, Rattle et al, Clin Chem, 30: 1457–61 (1984) or fluorescent substance (see, for example, U.S. Pat. No. 4,115,535 to Giaever; Moscoso et al., Clin. Chem., 34: 902–05 (1988); R. D. Nargessi et al., J. Immunol. Meth., 71: 17–24 (1984); and Kamel et al., Clin. Chem., 26: 1281–84 (1980)) as the reporter substance. The use of this methodology to separate certain subpopulations of lymphocytes from bone marrow cells prior to transplantation and to eliminate post-transplantation graft vs. host reaction, has also been reported. See A. Butturini et al., Prog. Bone Marrow Transpl., 413–22 (1987). Other reported uses of this technology include the separation of tumor cells (see: Kemshead et al., B. J. Cancer, 54: 771–78 (1986)) and the separation of lymphocyte subpopulations for subsequent functional evaluation (Berman et al., supra).

The application of magnetic affinity cell separation to the quantitation of lymphocyte subsets in blood has been reported. See J. Brinchmann, Clin. Exp. Immunol., 71: 182–86 (1988) and references cited therein. In this procedure, blood samples were incubated with superparamagnetic polymer microspheres coated with monoclonal antibodies specific for distinct lymphocyte subpopulations. The cells bound to the microspheres were isolated from the rest of the population by applying a magnetic field to the sample. The separated cells were then lysed to detach them from the microspheres, the microspheres and attached cell membranes were magnetically removed, and the resulting cell nuclei were stained and counted manually with a fluorescent microscope and hemocytometer. The number of nuclei counted corresponded to the number of cells in the sample in the subpopulation of interest. While this procedure may be used to enumerate the cells in a subpopulation of interest, manual enumeration of the cell nuclei is very time consuming and susceptible to technical error in sample loading of the hemocytometer and counting. Such a procedure would not be suitable for use in a clinical setting.

A need exists, therefore, for improved methods to determine the presence or quantity of particular subpopulations of cells within a mixed cell population such as that which comprises whole blood. The characteristics of such improved methods should include: sensitivity comparable to or greater than methods heretofore available, ability to analyze samples comprising a plurality of cells in a relatively brief time, and elimination of the need for expensive equipment and highly skilled personnel to perform the method.

SUMMARY OF THE INVENTION

The present invention provides a convenient, reliable and relatively inexpensive method for conducting analyses of various particulate analytes, e.g., human cells. The method of the invention involves analyte-specific interaction between a pair of reagents, comprising a detection reagent and a separation reagent, and a characteristic determinant associated with the particulate analyte at spaced apart locations on the surface thereof. The preferred embodiment of this method is independent of the concentration or density of the characteristic determinant on the analyte particles, which can vary from one analyte to another, or from particle to particle within a single analyte.

The separation reagent used in the practice of this invention comprises an insolubilized phase for facilitating separation from the test sample of analyte particles that become attached thereto in performing the present method. A specific binding substance that binds specifically to a characteristic determinant of the analyte is affixed to the insolubilized phase.

The detection reagent comprises a detectable label in particulate form which is also preferably associated with an insolubilized phase. The detection reagent also comprises a specific binding substance that binds specifically to a characteristic determinant of the analyte, which may be the same as or different from the determinant which is bound by the specific binding substance associated with the separation reagent. The detection reagent, when unbound, must be separable from the analyte-bound detection reagent via the analyte-bound separation reagent. It must also be separable from the unbound separation reagent. This enables quantitation of the analyte concentration via monitoring either the analyte-bound or unbound detection reagent.

In carrying out the method of the present invention, the detection reagent and separation reagent are added substantially simultaneously to the sample containing the analyte of interest. The amounts of added separation and detection reagent should be sufficient to substantially completely cover the surfaces of the analyte particles, thereby to form rosettes. The ratio of added separation reagent to added detection reagent should be such as to effect separation of a constant or fixed fraction of said rosettes and render said separated rosettes detectable. Preferably, the method is carried out under conditions whereby the rosettes are substantially completely separable from the sample.

The sample is thereafter subjected to conditions promoting rosette formation between the separation and detection reagents and the analyte particles and the resulting rosettes are separated from unbound detection reagent.

The label in either the separated rosettes or in the separated unbound detection reagent is then measured, the measurement being determinative of the presence or concentration of the particulate analyte in the sample.

According to a particularly preferred embodiment, the method of the present invention is performed on whole blood for lymphocyte subset monitoring of AIDS patients. This embodiment of the invention is performed by adding to a sample of whole blood an admixture of the aforementioned separation reagent and detection reagent. In this embodiment, the separation reagent comprises finely divided, magnetically responsive particles, to which are affixed monoclonal antibody that binds specifically to a cell surface antigen on the lymphocytes of interest, e.g., anti-CD4 or anti-CD8. The diameter of separation reagent particles with antibody affixed thereto should be at least 0.1 microns. The detection reagent also comprises a finely divided particulate support, but one which is nonmagnetic and bears a detectable fluorescent substance. The detection reagent is rendered immunologically reactive toward the target lymphocyte by affixing thereto monoclonal antibody that binds specifically to an antigen on the lymphocytes of interest, preferably the same antigen to which the separation agent specifically binds. The diameter of the fluorescence substance-bearing particles comprising the detection reagent should be at least 0.1 microns.

The amounts of the added separation and detection reagents should be sufficient to substantially completely cover the surfaces of the lymphocytes of interest, so as to form rosettes, with the detection reagent generally comprising about 30 to 70 percent of the assay reagent solid phase components, by particle count, weight or concentration (depending on the nature of the reagent). The solid phase which constitutes the separation system comprises the remaining 30 to 70 percent of the solid phase assay components.

The resulting sample is then subjected to conditions causing rosette formation between the separation and detection reagents and the lymphocytes of interest, after which the rosettes thus formed are magnetically separated from the non-magnetic components of the test sample.

The separated rosettes are then washed to remove unbound detection reagent and the label in the separated rosettes is measured, the measurement being determinative of the presence or concentration of the lymphocytes of interest in the blood sample.

According to another aspect of the invention, a test kit is provided for performing the method of the invention. Such a test kit may include various components depending on the nature of the cells sought to be determined. A test kit would typically comprise primary assay reagents consisting of containers of detection and separation reagents specific for the target cell type, as well as containers of detection and separation reagents which are not targeted to a specific cell type, as non-specific binding control reagents. Separate containers of calibrator reagents would also be provided. Assay plates and a set of user instructions would also typically be included in the kits. The test kits may also include other accessories useful in carrying out the methods of the invention.

The method of the invention may be used as an adjunct to, and in certain instances as a replacement for, the above noted analytical techniques currently applied in clinical laboratories, whose purpose is to screen for changes in cell frequency, viz., flow cytometry or fluorescence microscopy. The methods described herein utilize multiparametric measurement, which previously was limited to flow cytometric analysis, while substantially reducing the time burden inherent in flow cytometry. Moreover, unlike flow cytometry, the methods of the invention do not require complex, expensive equipment and highly skilled personnel.

The method of the invention has other decided advantages over the prior art. Thus, the cell subset of interest may be reliably quantitated from whole blood in the clinical setting without extraneous analysis. Other methods for determining the absolute concentration of cells in a subset of interest utilize two or more different measurements to obtain the value of interest. For example, flow cytometry measures the proportional number, rather than absolute number of lymphocytes of interest in a sample. To obtain the absolute blood concentration of a cell type of interest (e.g., CD4 lymphocytes), the following calculation must be made:

$CD4$ lymphocytes per liter blood=(% $CD4$) lymphocytes)×(% lymphocytes in white blood cells)×(#white blood cells per liter blood)

Such an analysis requires three sets of measurements: flow cytometry, white blood cell count, and differential white cell count. Typically, the flow cytometric analysis is performed in an immunology laboratory while the white blood cell and differential counts are performed in a hematology laboratory. These may be different laboratories within the same facility or may be located at different facilities. However, the data from both laboratories must be compiled in order to obtain the results which are reported to the clinician.

The reliability of such cytometric analysis is essential for proper diagnosis. For example, the decision of whether to initiate azidothymidine (AZT) therapy in AIDS patients rests on a measurement of the number of CD4 lymphocytes per liter of the patient's blood. If this number falls below $0.500 \times 10^9$ CD4 cells per liter, AZT therapy is recommended. See State-of-the-Art conference on Azidothymidine Therapy for Early HIV Infection, Am. J. Medicine, 89: 335–44 (September 1990). Since flow cytometric analysis involves the calculations described above, any alteration in the fraction of lymphocytes in blood will cause an error in the calculated CD4 lymphocyte concentration. Neutrophils, which typically comprise half or more of the white blood cells, are fragile and may degrade during specimen storage or transport to the clinical laboratory. A decrease in the fraction of neutrophils in the white blood cells would cause a concomitant increase in the measured fraction of lymphocytes, and thus a potentially erroneous measurement of CD4 lymphocytes per liter of blood. Such a result could lead a physician to recommend against AZT therapy when, in fact, the patient should be receiving it.

Furthermore, the methods of the invention provide a bulk assay technique for directly quantitating analytes of interest in a given biological sample, i.e., no correlation of an antigen's total expression with a cell concentration is required.

Other advantages of the present invention will be apparent to those skilled in the art upon consideration of the drawings in conjunction with the detailed description of the invention presented below.

BRIEF DESCRIPTION OF THE DRAWINGS

FIG. 2 is a schematic depiction of an assay for CD4-bearing target cells in which both the immunomagnetic separation reagent and immunofluorescent detection reagent are targeted to the CD4 antigen.

FIG. 4 shows the correlation between results obtained in lymphocyte assays using the method of the invention versus a reference method comprised of the combination of CDC/differential counting and flow cytometry.

DETAILED DESCRIPTION OF THE INVENTION

The present invention provides methodology for efficiently and reliably determining the presence or concentration of various particulate analytes, which may be any constituent of a particle nature that is present in a test sample or specimen, the presence of which analyte may be determined by selective interaction with a specific binding substance. The term "particulate analyte", as used herein, thus includes a variety of substances of potential biological or medical interest which may be measurable individually or as a group. Representative examples of "particulate analytes" include cells, both eucaryotic (e.g., leukocytes, erythrocytes or fungi) and procaryotic (e.g., bacteria, protozoa or mycoplasma), viruses, cell components, macromolecules and the like. Often it is desirable to determine the presence or quantity of a particular cell type for diagnostic or therapeutic purposes. Examples include the determination of leukocytes within a population of blood cells, helper T lymphocytes within a population of lymphocytes, fetal cells within maternal circulation, virus-infected cells within a population of uninfected and infected cells, or neoplastic cells within a population of normal and neoplastic cells. Although the method of this invention is useful for the determination of many different types of particulate analyte, it will be described hereinbelow with particular reference to the detection of human blood cells.

The foregoing analyte determinations can be performed using the method of the invention, which takes advantage of the phenomenon known in the field of hematology as "rosetting". Thus, when cells that express a characteristic determinant, e.g., a surface antigen are incubated with a saturating concentration of particulate reagent to which is affixed an antibody against the characteristic determinant, the target cells are rosetted by the particulate reagent. That is to say, the reagent particles completely coat the cell surface. As applied in the practice of this invention, the total number of reagent particles, i.e., detection reagent and separation reagent, which bind the cell type of interest is a function of the relative sizes of the reagent particles and cells and the total cell concentration.

The term "determinant" is used herein in its broad sense to denote an element that identifies or determines the nature of something. When used in reference to the method of the invention, "determinant" means that portion of an analyte which is involved in and responsible for selective binding to a specific binding substance, the presence of which is required for selective binding to occur.

The expression "characteristic determinant" when used herein in reference to cells, for example, signifies an epitope (or group of epitopes) that serves to identify a particular cell type and distinguish it from other cell types. Cell-associated determinants include, for example, components of the cell membrane, such as membrane-bound proteins or glycoproteins, including cell surface antigens of either host cell or viral origin, histocompatibility antigens or membrane receptors. Thus, in an analysis of lymphocytes according to the present invention, the characteristic antigen may be one or more of CD2, CD3, CD4, CD8, CD16, CD19, CD34 and CD56.

The expression "specific binding substance", as used herein, refers to any substance that selectively recognizes and interacts with a characteristic determinant on an analyte of interest, to the substantial exclusion of determinants present on analytes that are not of interest. One class of specific binding substances used to selectively interact with the above-mentioned cellular determinants are antibodies capable of immunospecifically recognizing same. Based on such selective recognition, the specific binding substance is capable of selective interaction and binding with a cell type of interest to form rosettes that are physically separable from the test medium and other components therein which are not of interest.

The term "antibody" as used herein includes monoclonal or polyclonal immunoglobulins and immunoreactive immunoglobulin fragments.

Representative examples of characteristic determinants and their specific binding substances are: receptor-hormone, receptor-ligand, receptor-agonist, receptor-antagonist, Protein A-IgG Fc component, Protein G-IgG Fc component, avidin-biotin, receptor-virus and receptor-lectin.

Analytes of potential biological or medical interest may be present in test samples or specimens of varying origin, including biological fluids such as whole blood, serum, plasma, saliva, urine, cerebrospinal fluid, amniotic fluid, lavage fluids and tissue extracts. The methods of the invention may also be performed on other test samples of interest, including environmental waters, e.g., waste water, well drilling fluids, and the like.

Cell types that are determinable in accordance with the present invention include cells of human or animal origin or cultured cells. Of particular interest in diagnostic, therapeutic and research applications are lymphocytes, including B cells, T cells and recognized T cell subsets, such as helper T cells or suppressor/cytotoxic T cells. Different lineages of cells are characterized by expression of characteristic antigens or ligands. For example, B cells from mammalian blood samples express a number of surface antigens distinct from those expressed by T cells from the same sample. Quantitation of one cell type from a sample may be important in assessing certain pathological conditions. In the case of an individual infected with human immunodeficiency virus (HIV), blood tests are conducted for T helper cells bearing CD4 glycoprotein for purposes of determining the stage of disease and monitoring treatment. As discussed earlier, direct measurement of these cells at the time the sample is taken is important for the accurate assessment of the condition of the patient. As another example, an abnormally large proportion of a single B cell clone in a patient's blood may be indicative of a leukemic condition.

Cells from the same lineage at different stages of differentiation are also distinguishable by expression of characteristic antigens or ligands. For example, as a B lymphocyte develops from a stem cell to a pre-B cell and ultimately to a mature B cell, the cell membrane markers change in a predictable manner as the cell matures. A mature B cell expresses immunoglobulins as ligands on the cell membrane, whereas a pre-B cell expresses only cytoplasmic immunoglobulin heavy chains, which provides the basis for differential reactivity of these cell subsets, permitting subsequent determination.

Differential expression of ligands can further provide a basis for assessing pathogenesis such as viral infection. Virally infected cells may express viral markers which are absent from uninfected cells within the cell population.

The two principal reagents used in performing the assay of the invention are a separation reagent and a detection reagent. A set of calibration reagents are also beneficially employed in performing this assay, as will be discussed below.

The separation reagent comprises an insolubilized or solid phase that facilitates separation of target analyte from the test sample. The separation reagent also comprises a specific binding substance capable of binding specifically to a characteristic determinant of the analyte.

The insolubilized phase of the separation reagent is preferably a particulate magnetic material. Suitable particulate magnetic materials are those exhibiting ferromagnetism, paramagnetism or superparamagnetism, the latter material becoming magnetized only upon exposure to a magnetic field. Such magnetic materials may be impregnated or embedded in, or coated on or by various organic or inorganic materials. Suitable organic particulate supports include biocompatible homopolymers, e.g., polystyrene and co-polymers, e.g., styrene-acrylate. Ceramic materials of diverse composition may also be used as the insolubilized phase of the separation reagent. The chemical composition of the particulate support for the separation reagent is not critical, apart from the requirement that it be compatible with biological analytes. The separation reagent may be prepared from any material to which protein may be absorbed or covalently coupled, either directly or indirectly. According to a preferred embodiment, the separation reagent is an immunomagnetic particle capable of binding specifically to a characteristic determinant of the analyte of interest. Particularly preferred are polymeric spheres enveloping or coated with magnetic material.

The detection reagent is in particulate form, comprising a detectable label and a specific binding substance that binds specifically to a characteristic determinant of the analyte of interest.

The expression "detectable label" is used herein to refer to any substance whose detection or measurement, either directly or indirectly, by physical or chemical means, is indicative of the presence of the analyte of interest in the test sample. Representative examples of useful detectable labels include, but are not limited to, the following: molecules or ions directly or indirectly detectable based on light absorbance, fluorescence, reflectance, light scatter, phosphorescence, or luminescence properties; molecules or ions detectable by their radioactive properties; and molecules or ions detectable by their nuclear magnetic resonance or paramagnetic properties. Included among the group of molecules indirectly detectable based on light absorbance or fluorescence, for example, are various enzymes which cause appropriate substrates to convert, e.g., from non-light absorbing to light absorbing molecules, or from non-fluorescent to fluorescent molecules.

According to a preferred embodiment of the invention, the detectable label is incorporated into a particulate, insoluble support or carrier. Particularly preferred are polymeric spheres impregnated with fluorescent dyes. However, detectable macromolecules that are intrinsically particulate may be used if desired.

Specific binding substance may be conveniently affixed to a particulate material (solid phase or insoluble fluid phase) according to techniques well known in the art. Suitable techniques for this purpose include cross-linking, covalent binding or physical adsorption. A procedure for coupling specific binding substances to a magnetic solid phase, e.g., particulate magnetite, is described in E. Menz et al., Am. Biotech. Lab. (1986).

In preparing the assay reagents, a primary specific binding substance may be used in conjunction with a secondary or auxiliary specific binding substance which is capable of interacting selectively with the primary specific binding substance and which is affixed to a particulate support. Representative primary and auxiliary specific binding substances useful for this purpose are: murine antibody/Protein A affixed to a solid phase; murine antibody/anti-mouse immunoglobulin raised in another species and affixed to a solid phase; and biotinylated antibody/avidin affixed to a solid phase.

In practice, it has been found convenient to adsorb an auxiliary antibody (e.g., rat anti-mouse IgG1 specific) onto the particulate support, followed by capture of the primary antibody which is specific to the characteristic determinant on the analyte of interest. Preparation of assay reagents in this way has three advantages. First, it allows the use of the same "core particle" in the preparation of various different cell-specific reagents. Second, isotype-specific capture optimizes the presentation of the active binding sites for the cell-specific antibodies. Third, the auxiliary antibody provides a functional spacer between the particulate support and the specific antibody, which is believed to improve the binding of the reagents to cells. Alternatively, a cell-specific antibody could be covalently conjugated to a particulate support through a previously covalently conjugated spacer molecule. The length of such a spacer could be varied as desired, depending on the analyte sought to be determined.

The binding specifity (rat anti-mouse IgG1 specific) and nature (monoclonal/polyclonal) of the auxiliary antibody is not critical. The isotype specificity could be changed, i.e., IgG2a, to match the isotype of a different cell-specific antibody. Furthermore, the auxiliary antibody could be produced in a different species (e.g., chicken or rabbit). Moreover, there is no special requirement that the auxiliary antibody (or the cell-specific antibody) be monoclonal. A polyclonal goat anti-mouse serum would be expected to produce comparable results.

The specific binding substance incorporated in the separation reagent and the detection reagent should be directed against the same characteristic determinant on the analyte of interest, so that the labelling of the target analyte is independent of antigen density above a minimum threshold, thereby achieving the most accurate quantitation.

According to the preferred embodiment of the invention exemplified below, which involves cell monitoring based on immunological interaction between target cells and separation and detection reagents, the antibodies bound to the reagents are directed against the same target antigen, so as to maintain the antigen density independence of the analysis. Of course, the methods of the invention may be carried out with reagents comprising antibodies directed against different characteristic antigens on the cell types of interest and enable qualitative cell determinations, provided the target antigens are stably and uniformly expressed. Even if the target antigens are not stably and uniformly expressed, the methods of the invention are nonetheless useful for the purpose of qualitative cell determinations.

Since the binding of a particulate reagent to a particulate analyte is dependent on multipe antigen-antibody interactions, it should be recognized that the efficiency of both labelling and separation will be dependent on achieving a specific threshold number of antigen-antibody interactions. Above this threshold, both labelling and separation will be antigen density independent and assay results will achieve the greatest accuracy. Consequently, the term "target analyte", as used herein, refers to those analyte particles possessing the target determinant above a threshold density defined by the ability of the assay reagents to successfully label and separate said analytes under the conditions of practice of the assay.

The particulate support for the separation and detection reagents may be of any relative size and density, so long as the diameter of the particles is relatively larger than the average spacing between the target characteristic determinants on the surface of the particulate analyte of interest. For purposes of cell analytes, the average inter-antigen spacing for any given antigen on any given cell type may be readily determined by a Scatchard binding analysis of the specific binding substance to the target cell type. For this analysis, the total number of binding sites for the specific binding substance is determined in a fixed concentration of target cells. With this information, the average inter-antigen spacing can be calculated.

As previously noted, the average diameters of the particulate separation and detection reagents are at least 0.1 microns, and may be as large as 10 microns. According to a particularly preferred embodiment, the particulate supports of both such reagents are of substantially uniform particle size, which is within the range of 4–6 microns.

Cell analysis in accordance with the methods of this invention is conveniently performed using an immunomagnetic separation reagent and a non-magnetic, immunofluorescent detection reagent in 96-well microtiter plates which are then read on a fluorescence reader. The results from the fluorescence reader are obtained as raw data (fluorescence signal per well). Calculations are then made to determine the absolute target cell counts of the test sample or specimen (reported in cells/mm$^3$).

The fluorescence reader used in carrying out the methods of the invention should be calibrated and operated according to the manufacturer's recommendations.

Working mixtures of the separation reagent, detection reagent and an isotype control reagent should be prepared daily, by mixing appropriate amounts of respective reagent, as will be discussed in further detail below. Ordinarily, the resulting working reagent mixture will be stable for up to five hours at 4°–8° C. Before preparing the working mixture, the containers of the individual reagents should be agitated to make sure the individual particles are suspended and well mixed.

The detection and separation reagents are added to a test sample in various amounts, depending on the nature of the analyte sought to be determined. The amount used must be sufficient to substantially completely cover the surfaces of the particulate analytes, thereby to form rosettes. The appropriate amount of each reagent for assaying a specific cell type can be determined by routine experimentation.

The term "rosette" is a term of art well known in the field of biology, which is used to refer to a cell analysis technique in which surface structures are determined by interaction with indicator particles (typically erythrocytes) to form a group of cells consisting of a centrally located cell of interest which is surrounded by adherent indicator particles. The phenomenon of rosetting is to be distinguished from agglutination, the latter term referring to a process involving the formation of clumps or networks of cells or microorganisms, due to immunological interaction between cell-surface antigens and antibodies.

The relative amounts of detection reagent and separation reagent used in carrying out the method of the invention should be such as to effect separation of a fixed fraction of the analyte of interest and produce a fluorescent signal with adequate sensitivity. It is particularly preferred that substantially complete separation of the analyte of interest be effected. Separation of the analyte of interest is considered to be substantially complete when greater than 95 percent of the analyte of interest is removed from the sample by the separation system, as can be determined by flow cytometric analysis of the remainder of the sample.

The assay of the invention is performed by adding to a test sample, substantially simultaneously, the above-described separation reagent and detection reagent in the relative amounts previously noted. Substantially simultaneous addition of the primary assay reagents to the sample is essential in order to form rosettes having appropriate amounts of reagents bound thereto, so as to make the analyte both separable and detectable. If the detection reagent and separation reagent are added serially over an interval of time sufficient for the first added reagent to substantially cover the surface of the analyte of interest, an accurate measurement of the analyte concentration is not possible. The preferred practice, therefore, is to premix the detection and separation reagents, at the optimum ratio as determined in Example 2, below, to form a working reagent mixture.

The sample containing the added primary reagents is incubated, generally at a temperature of about 4° C. to about 37° C., or possibly higher depending on the nature of the target cells (mammalian versus non-mammalian), and the denaturation temperature of the antibody used as the specific binding substance. Typically, incubation is carried out at a temperature of about 15° to about 25° C. for a time sufficient to promote rosette formation between the primary reagents and the analyte particles. Generally, the time required for rosette formation is on the order of 5 minutes. The sample is generally agitated such that the analyte and particulate reagents remain uniformly mixed.

The resulting rosettes are separated from any unbound detection reagent and other potentially interfering matter present in the test sample. The separation step is facilitated by including magnetic material as a component of the separation reagent. Accordingly, separation may be readily performed using various commercially available magnetic separation devices. The term "separation", as used herein, includes the act of physically withdrawing one distinct phase from another (e.g., removal of solid phase from liquid phase), or the act of segregating two phases while the phases remain in contact, e.g., by magnetic sedimentation.

The label may be detected either in the separated rosettes or in the separated unbound detection reagent, the former procedure being preferred. The measurement thus obtained is determinative of the presence or concentration of the analyte of interest in the test sample.

The measured label may be correlated to a pre-determined standard. In a quantitative cell determination, for example, the amount of measured label is compared to the amount of label detected in, e.g., one or more pre-measured quantities of similarly labelled cells, so as to establish the absolute quantity of the cell type of interest in the sample.

Quantitative cell determinations usually involve the preparation of a standard curve, containing increasing known quantities of appropriately labelled cells. These known quantities of cells are plotted against the amount of measured label. Based on the standard curve, the quantity of cells comprising a particular cell type in the test sample may be derived from the amount of label detected therein.

Because quantitative cell determination may involve variable parameters, such as temperature dependent reagent activity and instrument assisted measurements, which may not be consistent from day to day, the cell standard curve must be calibrated against known quantities of detectable label. To this end, a linear series of calibration reagent is prepared from standard amounts of the detectable label, which is incorporated into the same particulate support used for the detection reagent. During the process of generating the standard curve, following separation, the known amount of detectable label present in the separated portion can be measured. By comparing the measurements of the cell standard curve with the predetermined standard quantity of the detectable label (i.e., calculate the ratio of the cell standard curve measurements to the slope of the calibration reagent line), a standard curve can be derived which is independent of the previously mentioned variable parameters. The absolute number of cells in an unknown sample can then be calculated from the ratio of the amount of detectable label in the unknown sample to the slope of the same linear calibration reagent and comparing the result to the standard curve.

The calibration reagents are prepared essentially as a dilution series of the particulate support to which the detectable label is attached, as will be discussed in the examples.

The reporter substance may be detected in several ways, well known to those skilled in the art. The quantity of detectable label in either of the above-mentioned separated components of the test sample is preferably determined directly from measurements using automated techniques.

A test kit for use in the practice of this invention would typically be comprised of: (1) containers of particulate detection reagent incorporating a specific binding substance directed to the target analyte; (2) containers of particulate separation reagent incorporating a specific binding substance directed to the target analyte; (3) a container of particulate detection reagent incorporating a non-specific binding substance as a non-specific binding control reagent; (4) a container of particulate separation reagent incorporating a non-specific binding substance as a non-specific binding control reagent; (5) one or more containers of assay calibration reagents consisting of various concentrations of the particulate labelling reagent used in the assay detection system; (6) 96-well assay plates or other appropriate containers (test tubes, etc.) in which to run the assay; and (7) a set of user instructions.

The following examples are provided to describe the present invention in further detail. These examples are intended merely to illustrate specific applications of the method of the invention and should in no way be construed as limiting the invention.

EXAMPLE 1

Preparation of Assay Reagents

Detection reagent and the separation reagent were prepared using substantially the same procedure, the essential difference between the reagents being the nature of the particulate support. Fluorescent polystyrene particles (Polyscience, Inc.) of 6 micron diameter were used as the particulate support for the detection reagent, whereas magnetite coated styrene-acrylate particles (Nippon Paint, Inc.) of 6 micron diameter were used as the particulate support for the separation system.

In each case the particulate supports were washed twice with a high pH protein-free buffer (0.1M boric acid, pH 8.5). The washed particles were then exposed to 200 µg/ml of a rat anti-mouse IgG1 isotype specific monoclonal antibody in the same wash buffer for 18–24 hours. The antibody adsorbed onto the surface of the particles. At the end of the incubation period, the free antibody was removed by several wash steps. The antibody-coated particles were then exposed to mouse antibodies of the IgG1 isotype directed against the appropriate cell type of interest, such as anti-CD4, anti-CD8 or non-specific IgG1 to provide a non-specific binding control reagent, for a period of two hours. The concentration of the solutions of monoclonal antibody directed against the target cell type were within the range of 20–100 µg/ml in the aforesaid high pH buffer, with 1% bovine serum albumin (BSA) added. At the end of the final incubation, the respective assay reagents were washed several times and resuspended to $2 \times 10^8$ particles/ml in the high pH buffer, containing 1% BSA.

The calibration reagents were prepared as a serial dilution of the particulate support to which the detectable label was attached. The particulate concentration of the high calibrator (C3) was adjusted such that the fluorescence intensity of a 100 microliter aliquot was three-fold brighter than a specimen containing 1000 CD4 cells/mm$^3$ of whole blood, when assayed with a matched set of primary reagents, as defined in Example 2. An aliquot of the high calibrator was diluted 2:3 to form the second calibrator (C2). The third calibrator (C1) was formed by diluting an aliquot of the second calibrator 1:2. The fourth calibrator (C0) was a buffer blank. The resultant calibrator series (C0, C1, C2, C3) exhibited a linear fluorescence intensity scale corresponding approximately to the signals generated by 0, 1000, 2000 and 3000 CD4 cells/mm$^3$ of whole blood.

EXAMPLE 2

Optimization of the Detection and Separation Reagent Mixture

To determine an optimal mixture of the detection and separation reagents, an inverse co-titration of the particulate reagents was done under assay conditions.

Stock suspensions of fluorescent and magnetic particulate reagents, prepared as generally described in Example 1 above, were made up to $3 \times 10^7$ particles/ml. Aliquots of each reagent type were then added to nine pairs of wells in a 96-well round bottom polypropylene plate, as listed below.

| Wells | Detection Reagent Volume (µl) | Separation Reagent Volume (µl) | % Fluorescent Beads |
|---|---|---|---|
| 1 & 2 | 0.00 | 50.00 | 0.0 |
| 3 & 4 | 6.25 | 43.75 | 12.5 |
| 5 & 6 | 12.50 | 37.50 | 25.0 |
| 7 & 8 | 18.75 | 31.25 | 37.5 |
| 9 & 10 | 25.00 | 25.00 | 50.0 |
| 11 & 12 | 31.25 | 18.75 | 62.5 |
| 13 & 14 | 37.50 | 12.50 | 75.0 |
| 15 & 16 | 43.75 | 6.25 | 87.5 |
| 17 & 18 | 50.00 | 0.00 | 100.0 |

The total volume of each particulate reagent mixture was 50 μl and the total reagent concentration (sum of fluorescent and magnetic reagents) in the well was $3 \times 10^7$ particles/ml.

Figure 2A:
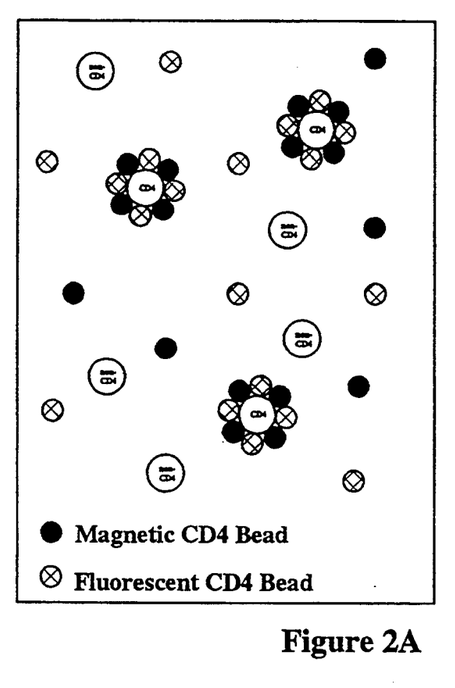
FIG. 2A depicts the binding step, in which both the detection and separation reagents simultaneously bind to the target cells, forming a rosette. At equilibrium, CD4-bearing cells are completely coated by the two reagents, while other cells are not.

50 μl of whole blood was then added to each reagent-containing well and the plate was placed on a conventional plate shaker for five minutes at room temperature. The speed was set such that it was high enough to keep the reagent particles suspended without shaking the blood out of the wells and to allow for specific reagent particle binding to the targeted cell population with minimal non-specific binding. FIG. 2A schematically depicts the equilibrium point in the binding reaction for the 1:1 mixture of magnetic and fluorescent beads. In FIG. 2A, it is assumed that the binding constants of each bead are the same. Although optimal performance is obtained when this assumption is met, this is not an absolute requirement for the assay methodology to perform adequately. CD4-expressing cells have been rosetted by the bead mixture. Non-CD4 cells are unbound and excess magnetic and fluorescent beads remain in suspension. In this experiment, specific binding of the reagent particles to the target cell population was confirmed by flow cytometric analysis of remaining cells in a cell depleted specimen after reagent treatment.

Figure 2B:
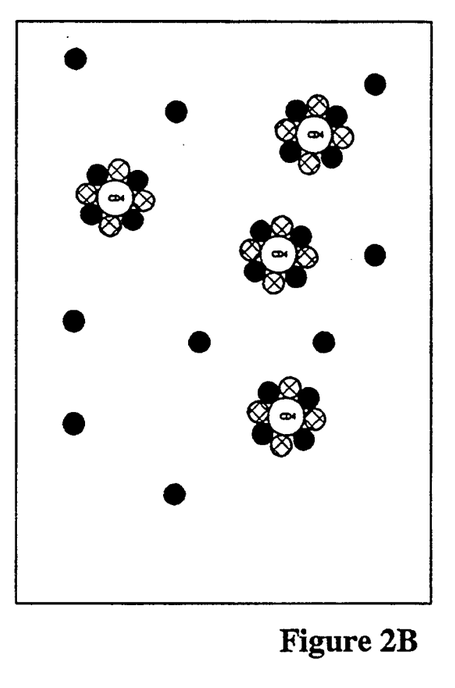
In FIG. 2B, the previously formed rosettes are depicted, washed free of non-target cells and unbound detection reagent, so that the only detection reagent remaining is bound to target cells, providing the means to quantify them.

Four magnetic washes were then employed to remove unbound cells and unbound fluorescent reagent from the wells. The 96-well plate was placed on a commercially available plate shaped magnet (Advanced Magnetics, Inc., Cambridge, Mass.) and the cell bound reagent allowed to sediment for 60 seconds. The supernatant was carefully removed by piper followed by removal of the plate from the magnet and resuspension of each well with 200 μl of phosphate buffered saline solution. This procedure was repeated 3 more times. FIG. 2B schematically depicts the resultant sample after magnetic washing. The unbound cells and unbound fluorescent reagent have been washed out of the sample, leaving rosetted target cells and excess magnetic reagent.

After the final buffer resuspension, the plate was placed in a conventional fluorescence plate reader and scanned. The CD4 and CD8 cell concentrations in the blood specimen were determined by multiplying the percent CD4 or CD8 lymphocytes in the specimen (determined by flow cytometry) by the lymphocyte concentration (determined by CBC differential counting). The measured fluorescence intensities were divided by the appropriate cell concentration (CD4 or CD8) and the results plotted versus the percent fluorescent beads. This plot is shown in FIG. 3.

The optimum bead mixture was determined to lie on the approximately linearly increasing up-slope of the optimization curve, displaying sufficiently high intensity per cell to give adequate sensitivity at cell concentrations of 1000 cell/mm$^3$ of whole blood for CD4 lymphocytes and 500 cell/mm$^3$ of whole blood for CD8 lymphocytes.

The specification that the optimum bead mixture be on the linear up-slope of the curve is a result of the preferred mode of practice in which the target analyte is substantially completely separated from the other components of the sample. Significant deviation from linearity indicates that separation of the target analyte is not substantially complete. Under these conditions, a fixed fraction of the analyte may still be separated, satisfying the absolute requirement for a quantitative assay. However, it is expected that the most accurate and stable assay results would be obtained when the separation is substantially complete.

Figure 3:
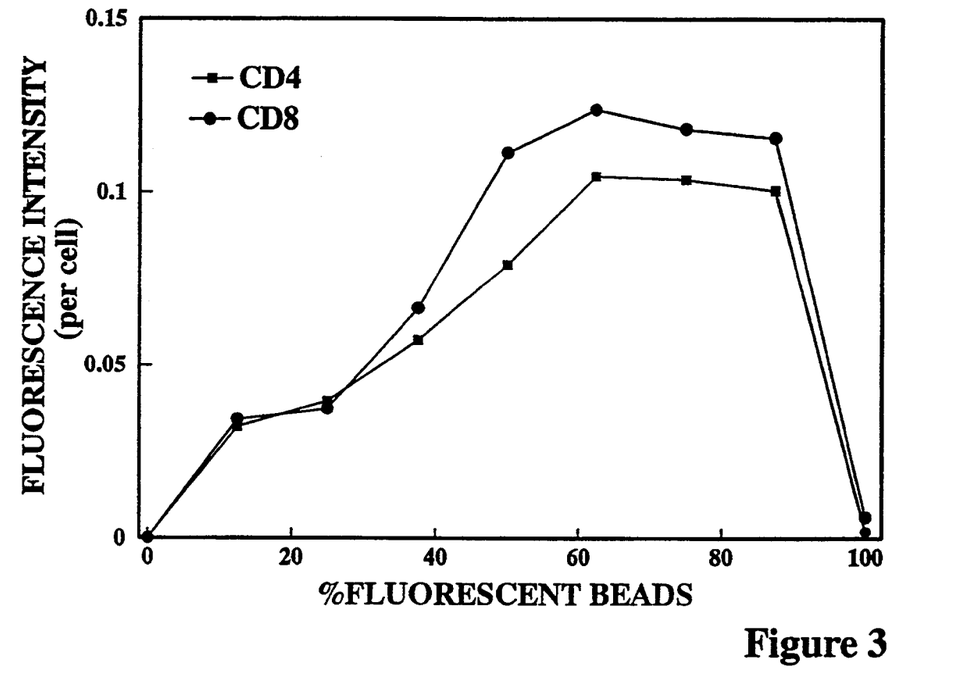
FIG. 3 is a graphic illustration of the determination of optimum ratio of non-magnetic, immunofluorescent detection reagent to immunomagnetic separation reagent for assaying lymphocytes, in accordance with the method of the invention, on the basis of CD4 or CD8 as the characteristic determinant.

Considering the data from FIG. 3, the optimum fraction of fluorescent reagent appears to be 37.5 or 50.0 percent fluorescent beads. Since a 1:1 mixture was considered easier to make-up, 50% fluorescent beads was chosen and used in the assays reported in Example 4, below.

EXAMPLE 3

Demonstration of Bead Rosetting Phenomenon

A 50 μl sample of whole blood was placed in a well of a 96-well round bottom polypropylene microtiter plate. 50 μl of a suspension of magnetic particle reagent, prepared as generally described in Example 1 above, at a concentration of $3 \times 10^7$ particles/ml, was added to the blood sample. The plate was placed on a conventional plate shaker for five minutes at room temperature. The speed was set such that it was high enough to keep the reagent particles suspended without shaking the blood out of the wells. Four magnetic washes were then employed to remove unbound cells from the well. The 96-well plate was placed on a commercially available plate shaped magnet (Advanced Magnetics, Inc., Cambridge, Mass.) and the sample was allowed to stand for 60 seconds. The supernatant was carefully removed by pipet followed by removal of the plate from the magnet and resuspension of the sample with 200 μl of phosphate buffered saline solution. This procedure was repeated 3 more times.

Figure 1:
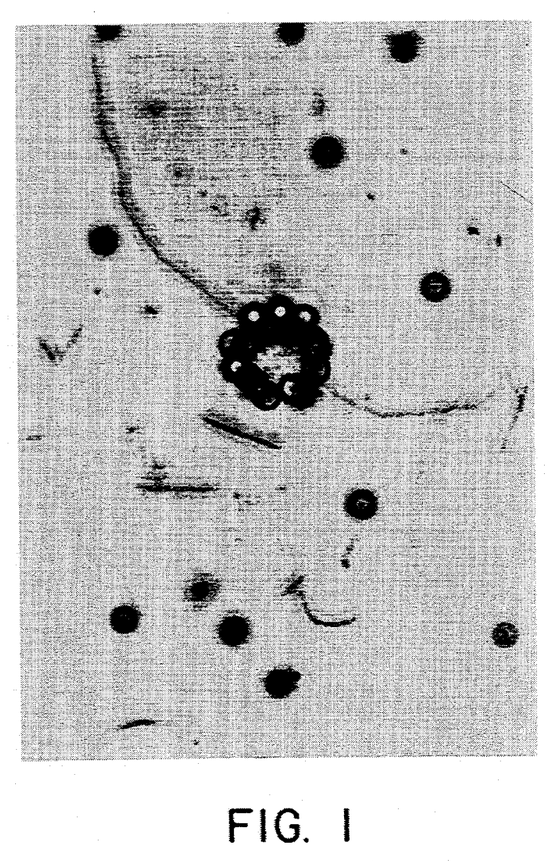
FIG. 1 is a photomicrograph which illustrates the principle of bead rosetting. The figure shows a rosetted CD4 lymphocyte after equilibrium binding with a CD4 immunomagnetic separation reagent, and magnetic washing to remove unbound cells.

After the final resuspension, a 10 μl aliquot of the sample was placed on a microscope slide and examined under the microscope using phase contrast optics. FIG. 1 shows a CD4 lymphocyte which has been rosetted (i.e., completely covered) by magnetic particle reagent affixed to anti-CD4.

EXAMPLE 4

Determination of Absolute CD4 and CD8 Lymphocyte Concentrations in Whole Blood Samples A. Calibration of the Assay In order to calculate the absolute cell concentration from a measured fluorescence intensity, the slope of the standard curve (i.e., the emitted fluorescence intensity per cell) must be determined. To do this, the emitted fluorescence intensity was measured for a series of whole blood samples which covered a wide cell concentration range (approximately 0–2000 cells/mm$^3$). The assay reagent mixture used for these measurements was the optimum mixture described in Example 2, above.

Stock suspensions of CD4 fluorescent and magnetic particle reagents at $3 \times 10^7$ particles/ml were mixed in a ratio of 1:1. 50 μl of this mixture was then added to the wells of a 96-well round bottom polypropylene plate. Similar mixtures of CD8 and non-specific isotype-matched control reagent were made and added to sets of separate wells. The later reagent type was used to control for non-specific binding of the CD4 and CD8 reagents. 50 μl of whole blood was then added to each reagent-containing well and the plate was placed on a commercially available plate shaker for five minutes at room temperature. The speed was set as previously determined in Example 2. Four magnetic washes were then performed as previously described to remove unbound cells and unbound fluorescent reagent. After the final buffer resuspension, a linear series of four calibration reagents was added to unused wells. The plate was again placed on the plate shaker for one minute to assure uniform suspension of all assay components. The plate was then placed in a conventional fluorescence plate reader and scanned.

The CD4 and CD8 cell concentrations in each blood specimen were determined by multiplying the percent CD4 or CD8 lymphocytes in the specimen (determined by flow cytometry) by the lymphocyte concentration (determined by CBC differential counting). For each specimen, the isotype control fluorescence intensity (non-specific binding signal) was subtracted from the CD4 or CD8 fluorescence intensity and the resultant values were divided by the slope of the linear reagent calibration curve, as shown below:

$$CD4 \text{ intensity} = (FI_{CD4} - FI_{IC})/S_{CAL}$$

$$CD8 \text{ intensity} = (FI_{CD8} - FI_{IC})/S_{CAL},$$

where $FI_{CD4}$, $FI_{CD8}$ and $FI_{IC}$ represent the fluorescence intensities measured in the wells corresponding to CD4, CD8 and the isotype matched non-specific binding control, respectively. $S_{CAL}$ represents the slope of the calibration reagent line. The calculated intensities, which are independent of the variable parameters, previously discussed, were plotted versus the appropriate cell concentrations. The slopes of the resulting standard curves were determined via regression analysis. These slopes represent the fluorescence intensity per unit cell concentration in the assay wells. The inverse of the standard curve slope values represent the proportionality constants (i.e., calibration factors) between the measured fluorescence intensity in an assay and the absolute cell concentration. These calibration factors are specific to each lot of reagents prepared for use in cell concentration assays.

B. Performing CD4 and CD8 Lymphocyte Concentration Assays

Stock suspensions of CD4, CD8 and isotype-binding control, fluorescent and magnetic particle reagents at $3 \times 10^7$ particles/ml were mixed in a ratio of 1:1. 50 µl of each mixture was then added to appropriate wells of a 96-well round bottom polypropylene plate. 50 µl of whole blood was then added to each bead containing well and the plate was placed on a commercially available plate shaker for five minutes at room temperature. The speed was set as previously determined in Example 2. Four magnetic washes were then performed as previously described to remove unbound cells and unbound fluorescent reagent. After the final buffer resuspension, the plate was placed in a commercially available fluorescence plate reader and scanned.

The absolute CD4 and CD8 cell concentrations were determined using the formulas shown below.

$$[CD4](\text{cell}/mm^3) = (FI_{CD4} - FI_{IC})/S_{CAL} * CD4 \text{ factor}$$

$$[CD4](\text{cell}/mm^3) = (FI_{CD8} - FI_{IC})/S_{CAL} * CD8 \text{ factor}$$

In these equations, $FI_{CD4}$, $FI_{CD8}$ and $FI_{IC}$ represent the fluorescence intensities measured in the wells corresponding to CD4, CD8 and the isotype matched non-specific binding control, respectively. $S_{CAL}$ represents the slope of the calibration reagent line. Finally, CD4 factor and CD8 factor represent the proportionality constants between the respective cell concentration and the assay result as defined by the calibrated standard curves, discussed previously.

Figure 4A:
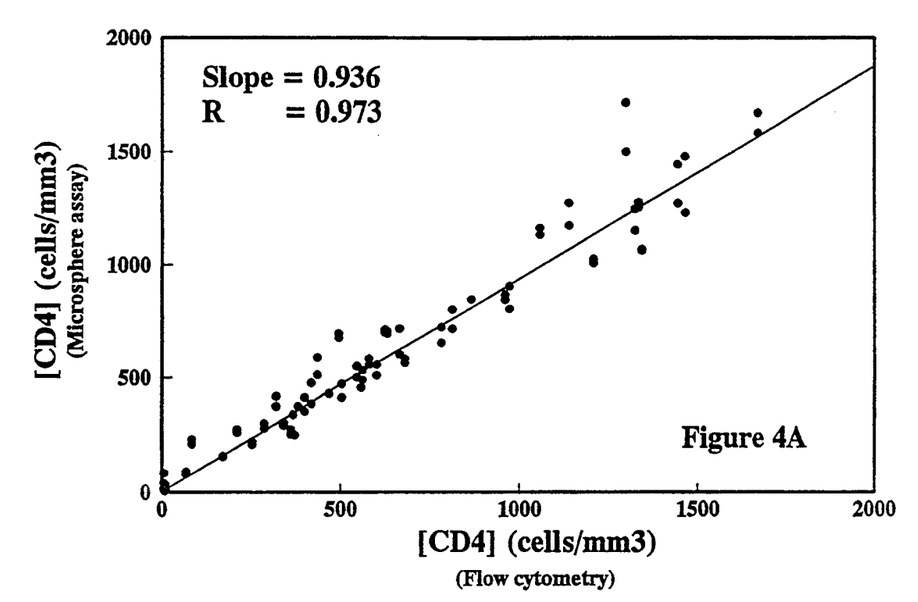
FIG. 4A sets forth the results of a CD4 lymphocyte assay.
Figure 4B:
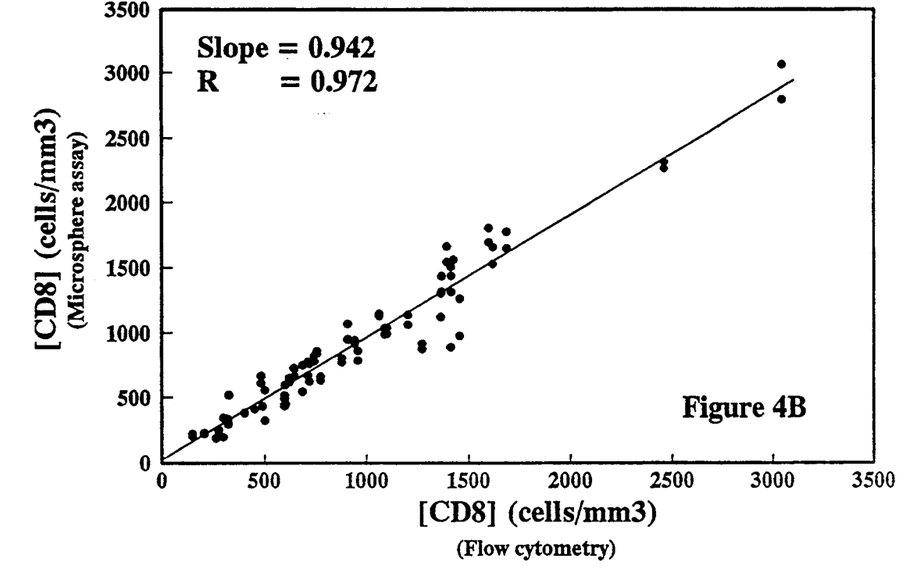
FIG. 4B sets forth the results of a CD8 lymphocyte assay.

In FIG. 4A and 4B, the calculated absolute CD4 or CD8 cell concentrations are compared to those measured by the flow cytometric reference method. For this reference method, the CD4 and CD8 cell concentrations in each blood specimen were determined by multiplying the percent CD4 or CD8 lymphocytes in the specimen (determined by flow cytometry) by the lymphocyte concentration (determined by CBC differential counting).

Although a preferred protocol for practicing the method of the invention has been described above, various alternative protocols can be utilized, if desired. For example, whole blood may be assayed for CD4-bearing lymphocytes, using immunomagnetic reagent particles targeted to the CD4 antigen and immunofluorescent reagent particles targeted to a coexpressed antigen, such as CD3 (T-cell antigen receptor). In the binding step, both fluorescent and magnetic reagent particles simultaneously bind to the target cells. At equilibrium, the CD4-bearing lymphocytes are rosetted with the primary assay reagents and CD8 lymphocytes are rosetted with the immunofluorescent reagent particles. All other cells are unbound. After magnetic sedimentation to wash out non-target cells and unbound detection reagent, the only detection reagent remaining in the test sample is bound to the lymphocytes of interest, providing the means to quantify them.

As another alternative, CD4- and CD8-bearing cells may be simultaneously determined in the same test sample. For each cell type of interest, immunomagnetic reagent particles and immunofluorescent particles are targeted to a single antigen. The detection reagent for the respective subtypes of interest must have an independently detectable label, i.e., each with a different fluorochrome having a distinctly different emission wavelengths. In the binding step, both the immunofluorescent reagent particles and the immunomagnetic reagent particles bind simultaneously to their respective target cells. At equilibrium, the CD4-bearing cells are rosetted with the CD4-directed reagents and the CD8-bearing cells are rosetted with the CD8-directed reagents. All other cells are unbound. After magnetic sedimentation to wash out non-target cells and unbound detection reagent, the only immunofluorescent detection reagent remaining in the sample is bound to the cell types of interest. Independent measurements at each emission wavelength are then made to simultaneously and individually quantitate the CD4 and CD8 cell concentrations.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope of the appended claims.

What is claimed is:

1. A method for determining the presence or concentration of particulate analyte in a sample, the particles comprising said analyte having at least one characteristic determinant on the surfaces thereof, the density of said determinant on any one analyte particle in said sample being the same as or different from the density of said determinant on any other said analyte particle, each said analyte particle having a multiplicity of said at least one characteristic determinant at spaced apart locations on the surfaces thereof, said method comprising the steps of:

a. adding to said sample, substantially simultaneously, a separation reagent and a detection reagent, said separation reagent comprising a particulate support having affixed thereto a specific binding substance that binds specifically to a characteristic determinant of said analyte, said particulate support facilitating separation of said analyte particles attached to said separation reagent from said sample, said detection reagent comprising a particulate support including a detectable label and having affixed thereto a specific binding substance that binds specifically to a characteristic determinant of said analyte, said detection reagent, when unbound, being separable from both said separation reagent and said detection reagent bound to said analyte; and said specific binding substance of said separation reagent and said specific binding substance of said detection reagent binding specifically to the same characteristic determinant, the diameter of said particulate supports of said separation and said detection reagents being larger than the average distance between said spaced apart characteristic determinants, the amounts of said added separation and detection reagents being sufficient to substantially completely cover the surfaces of said analyte particles, thereby forming rosettes, the ratio of said added separation reagent to said added detection reagent being such as to effect separation of a constant fraction of said rosettes and render said separated rosettes detectable;

b. subjecting said sample to conditions promoting rosette formation between said separation and detection reagents and said analyte particles;

c. separating said rosettes from unbound detection reagent; and d. measuring the label in said separated rosettes or in said separated unbound detection reagent, said measurement being determinative of the presence or concentration of said particulate analyte in said sample.

2. A method as claimed in claim 1, wherein the concentration of said particulate analyte is determined directly as a function of measured label.

3. A method as claimed in claim 1, wherein said particulate analyte comprises human cells and said at least one characteristic determinant comprises at least one cell surface antigen.

4. A method as claimed in claim 3, wherein said human cells are lymphocytes and said at least one characteristic antigen is selected from the group consisting of CD2, CD3, CD4, CD8, CD16, CD19, CD34, and CD56.

5. A method as claimed in claim 3, wherein said separation reagent comprises a magnetic particulate support, to which is affixed antibody that binds specifically to said at least one cell surface antigen.

6. A method as claimed in claim 5, wherein said antibody comprises monoclonal antibody.

7. A method as claimed in claim 5, wherein the diameter of said separation reagent is in the range of about 0.1 to about 10 microns.

8. A method as claimed in claim 3, wherein said detection reagent comprises a particulate polymer support bearing a fluorescent substance as said detectable label, to which is affixed antibody that binds specifically to said at least one cell surface antigen.

9. A method as claimed in claim 8, wherein said antibody comprises monoclonal antibody.

10. A method as claimed in claim 8, wherein the diameter of said detection reagent is in the range of about 0.1 to about 10 microns.

11. A method as claimed in claim 1, wherein the particulate supports of said separation and said detection reagents are of uniform size.

12. A method for determining the presence or concentration of a subset of lymphocytes in a blood sample, said lymphocytes having on the surfaces thereof at least one antigen selected from the group consisting of CD4, CD8, CD3, CD2, CD16, CD19, CD34, and CD56 antigens, the density of said at least one antigen on any one lymphocyte in said blood sample being the same as or different from the density of said at least one antigen on any other of said lymphocytes, the concentration of said lymphocyte subset sought to be determined being independent of said antigen density, said method comprising the steps of:

a. adding to said blood sample a reagent mixture comprising a separation reagent and a detection reagent; said separation reagent comprising finely divided, magnetically responsive particles, to which are affixed monoclonal antibody that binds specifically to one antigen of said group of antigens; said detection reagent comprising finely divided non-magnetic particles that bear a detectable fluorescent substance and to which are affixed monoclonal antibody that binds specifically to said one antigen of said group of antigens; the diameter of said magnetically responsive particles and the diameter of said fluorescent substance-bearing particles being at least 0.1 microns and being larger than an expected average distance between molecules comprising said one antigen of said group of antigens on the surfaces of said lymphocytes; and the amounts of said added separation and detection reagents being sufficient to substantially completely cover the surfaces of said lymphocytes, thereby forming rosettes, said detection reagent comprising about 30 to about 70% and said separation reagent comprising the remaining about 30 to about 70% by particle count, of said reagent mixture;

b. incubating the sample from step a. at a temperature in the range of about 4° C. to about 37° C. for a time sufficient to cause rosette formation between said separation and detection reagents an said lymphocytes;

c. magnetically separating the resultant rosettes from the non-magnetic components of said sample;

d. washing said separated rosettes to remove therefrom unbound detection reagent; and e. measuring the label in said washed rosettes, said measurement being determinative of the presence or concentration of said lymphocites in said blood sample.

13. A method as claimed in claim 12 wherein the antibody of said separation reagent and the antibody of said detection reagent bind specifically to CD4 antigen.

14. A method as claimed in claim 12, wherein the antibody of said separation reagent and the antibody of said detection reagent bind specifically to CD8 antigen.

* * * * *